US009477100B2

(12) United States Patent
Podrow et al.

(10) Patent No.: US 9,477,100 B2
(45) Date of Patent: Oct. 25, 2016

(54) RADIATION FILTRATION SHIELDS FOR EYE OR BODY PROTECTION

(71) Applicant: ViewMax Solutions LLC, Fayetteville, AR (US)

(72) Inventors: Anthony Steven Podrow, Maple Ridge (CA); Christopher Lynn Owens, Fayetteville, AR (US)

(73) Assignee: ViewMax Solutions LLC, Fayetteville, AR (US)

( * ) Notice: Subject to any disclaimer, the term of this patent is extended or adjusted under 35 U.S.C. 154(b) by 0 days.

(21) Appl. No.: 14/502,700

(22) Filed: Sep. 30, 2014

(65) Prior Publication Data

US 2016/0091735 A1 Mar. 31, 2016

(51) Int. Cl.

*G02C 9/04* (2006.01)
*G02C 7/10* (2006.01)
*G02C 7/16* (2006.01)

(52) U.S. Cl.

CPC . *G02C 9/04* (2013.01); *G02C 7/10* (2013.01); *G02C 7/104* (2013.01); *G02C 7/16* (2013.01)

(58) Field of Classification Search

CPC ........ G02C 7/08; G02C 7/086; G02C 7/088; G02C 7/10; G02C 7/104; G02C 9/00; G02C 9/04; G02C 2200/08

USPC ............... 351/47, 48, 57, 58, 159.6, 159.63, 351/159.65

See application file for complete search history.

(56) References Cited

U.S. PATENT DOCUMENTS 3,171,134 A * 3/1965 Kennedy .................. G02C 7/10 2/13
5,007,727 A * 4/1991 Kahaney .................. G02C 9/00 351/47

FOREIGN PATENT DOCUMENTS

FR 2517838 * 6/1983 ............... G02C 7/10

* cited by examiner

*Primary Examiner* — Huy K Mai
(74) *Attorney, Agent, or Firm* — Knobbe Martens Olson & Bear, LLP

(57) ABSTRACT

A radiation filter insert is provided. The glasses filter insert includes a first filter lens and a second filter lens, each having an inner surface and an outer surface. The first and second filter lens may include an electromagnetic filter. The present invention may include a bridge connector. The bridge connector may connect the first and second filter lenses together. The bridge connector may include a curved inner edge formed to fit around a nosepiece of an eyewear. The filtering insert may include resting tabs to allow the insert to remain in position on the eyewear. The filtering insert may further include grasping tabs. The grasping tabs allow placement using the thumb an index finger of one hand. These resting and grasping tabs enables insertion and removal without displacing the eyewear. Therefore, a user may wear a pair of protective glasses and may insert the radiation filter insert in between the protective eyewear and the user, thereby shielding the user from electromagnetic energy or enabling its screening qualities.

16 Claims, 3 Drawing Sheets

18
18
16
16
10
12
12
20
22
22
50
50
22
22
14
14

RADIATION FILTRATION SHIELDS FOR EYE OR BODY PROTECTION

CROSS-REFERENCE TO RELATED APPLICATION

This application claims the benefit of priority of U.S. provisional application No. 61/859,976, filed Jul. 30, 2013, the contents of which are herein incorporated by reference.

BACKGROUND OF THE INVENTION

The present invention relates to a radiation filter and, more particularly, to a radiation filter used in conjunction with eyewear.

Currently, most laser eye protection includes either safety glasses, goggles, or clip in glass filters that clamp onto existing eyewear. Goggles do not work with magnification loupes or telescopes or eyewear mounted light sources and are difficult to use with prescription glasses. Safety glasses cannot be effectively used in conjunction with regular eyewear. The clip on glass filter inserts utilizes metal clamps and springs and mounts on the front of the user's eyewear. This clip on glass filter is not useable for eyewear with curved frames (currently more popular than straight frames) or with magnification telescopes which traverse through the lenses of the eyewear. Other glass filters available mount on the inside of the user's eyewear. This may enable use with "through the lens telescopes" but the glass filters most likely impinge upon these telescopes. These clip in filters rely on a complicated clip on, clip off mechanism of metal clamps to affix them and they have no specific "handles" to aid in their manipulation. This creates several significant problems in that the user (a dentist, for example) upon requiring the use of the filtering device, must remove used gloves, remove the eyewear from the face, and use both hands to affix the filtering device. The user must then reposition the eyewear on the face and re-glove before continuing with his/her procedure. Upon finishing the procedure that required the filtering device, he/she must again remove the used gloves, remove the eyewear, use both hands to remove the filtering device from the eyewear, replace the eyewear back on the face, and then again re-glove in order to continue treatment. This is very cumbersome and time consuming as well as requiring the practitioner to spend more money for consumable supplies such as gloves, while creating a fogging effect for many practitioners. Less conscientious practitioners may be inclined to bypass the steps of removing and replacing gloves twice; which would be unhygienic and lead to the additional problem of risk of infectious cross-contamination. Furthermore, these glass inserts with clamps are awkward to disinfect. Additional disadvantages of the clip in filter inserts are that they are heavy, expensive, prone to fogging, and do not fully surround and protect the eyes from stray laser flashes which could lead to eye damage.

As can be seen, there is a need for a less expensive, easier to use, lighter weight no fog radiation filtering device or insert that prevents potential eye damage when working with instruments that emit radiation.

SUMMARY OF THE INVENTION

In one aspect of the present invention, a filtering insert comprises: a first electromagnetic filter lens comprising an inner surface and an outer surface; a second electromagnetic filter lens comprising an inner surface and an outer surface; a bridge connector connecting the first electromagnetic filter lens and the second electromagnetic lens, and comprising a curved inner edge formed to fit around a nosepiece of an eyewear; and at least one resting tab extending from an edge of the filtering insert and protruding past the outer surfaces of the first and second electromagnetic filter forming a channel, wherein the channel is sized to secure over a frame of the eyewear.

In another aspect of the present invention, a method of protecting eyes from damage comprising: placing a pair of eyewear on a user; and placing a filtering insert in between the eyewear and the user, wherein the filtering insert comprises a pair of electromagnetic filter lenses.

These and other features, aspects and advantages of the present invention will become better understood with reference to the following drawings, description and claims.

DETAILED DESCRIPTION OF THE INVENTION

Figure 1:
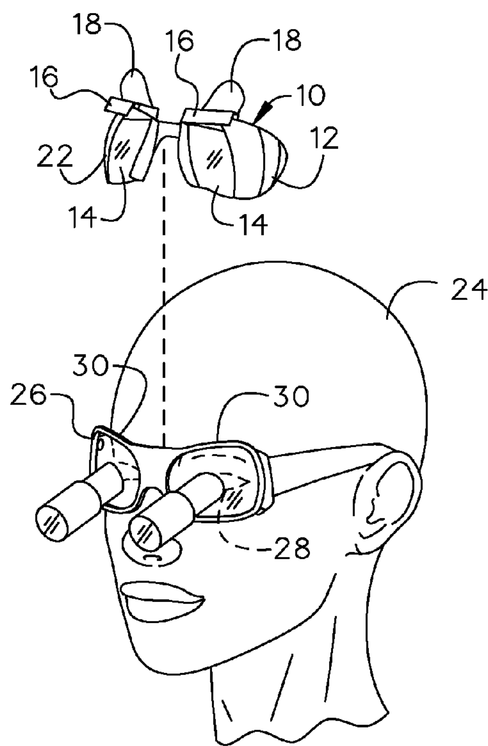
FIG. 1 is an exploded view demonstrating the present invention's application.
Figure 2:
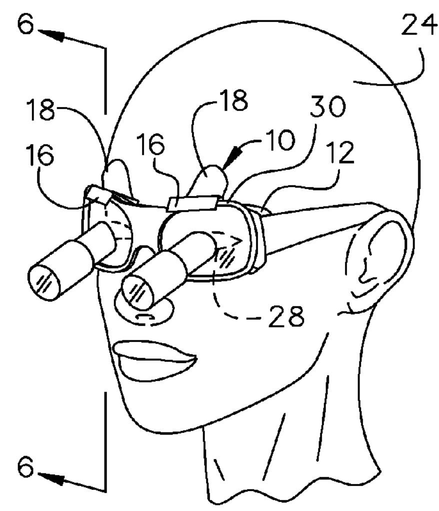
FIG. 2 is a perspective view of the present invention shown in exemplary usage.
Figure 3:
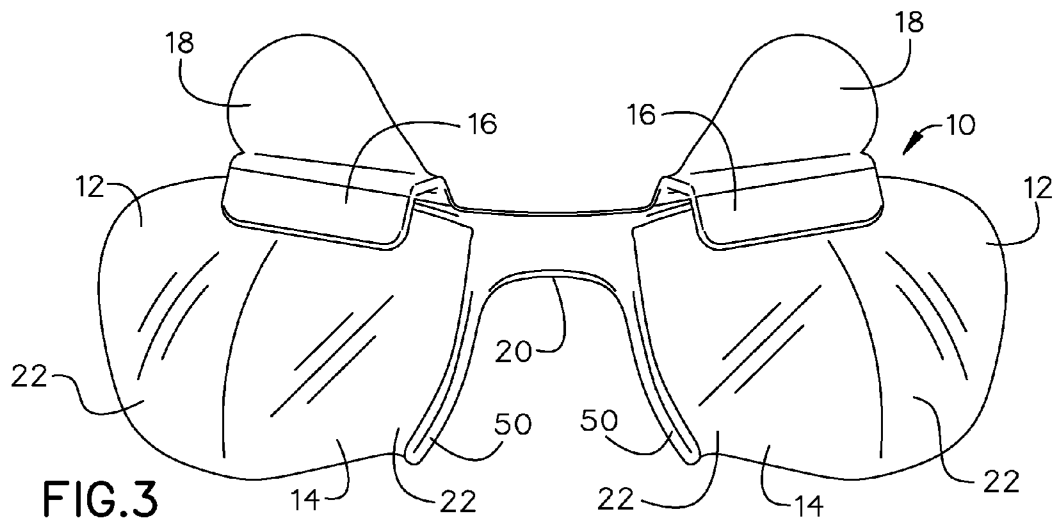
FIG. 3 is a front view of the curved embodiment of the present invention.
Figure 4:
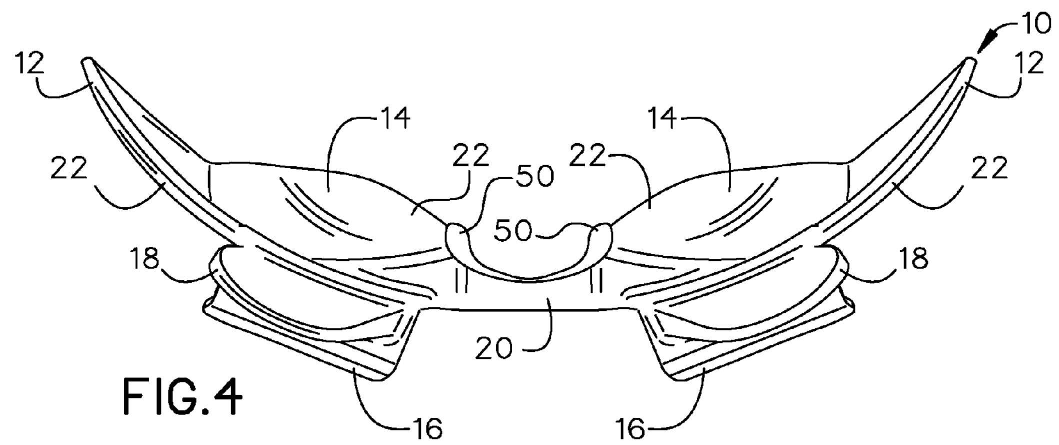
FIG. 4 is a top view of the curved embodiment of the present invention.
Figure 5:
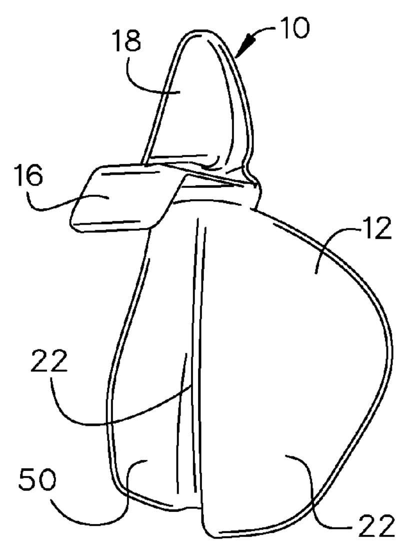
FIG. 5 is a side view of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes several objects and advantages which solve the above mentioned problems with the prior art. The present invention is designed in different embodiments to fit curved-framed eyewear or straight-framed eyewear. The present invention fits onto the eyewear frames between the eyewear and the user's face; therefore they work well with "tip-up magnification loupes" or the popular "through the lens magnification telescopes" and do not interfere with eyewear mounted light sources. The right and left filtering lens channels may be recessed to prevent impingement of the telescopes which traverse through the eyewear lenses onto the radiation filter. The wide recesses accommodate large variations of interpupillary widths and through the lens telescope diameters. Therefore the present invention accommodates wide or narrow as well as high or low telescope placement in the magnification eye wear lenses. The present invention does not require metal clamps to hold it in place. The retention relies on gravity and the forward slope of the human cheeks specially designed "resting tabs" (which rest on the anterior portion of the eyewear frame), and the medial and lateral filtering protective barriers which stabilize the filter inserts into position. The present invention may also include a grasping tab above both the right and left filtering lenses which enables the user to ease the filtering device into position using just the thumb and index finger of one hand (either right or left) without needing to remove the eyewear from the face. This also eliminates the time, nuisance, and necessity of removing and replacing gloves twice; as only the grasping tab(s) are touched. The tab itself could be temporarily protected with a bit of cellophane or a sterile gauze or wiped down with a cold sterile disinfectant after use. Therefore the risk of cross contamination between patients is vastly reduced to the point of being virtually eliminated. The filtering material of choice with most electromagnetic sources will likely be polycarbonate or plastic which adds the benefits of being lighter, fog resistant, and extremely resistant to breakage as well as making the products simpler to manufacture and use, as well as being considerably less expensive than the traditional glass filters that have been used in the past. Additionally the user's eyes are virtually surrounded by protective barriers and are more comprehensively protected from stray or scatter radiation; which provides better protection against eye damage or blindness.

The present invention is an electromagnetic radiation filtering or partial filtering insert that fits upon the user's eyewear.

Figure 6:
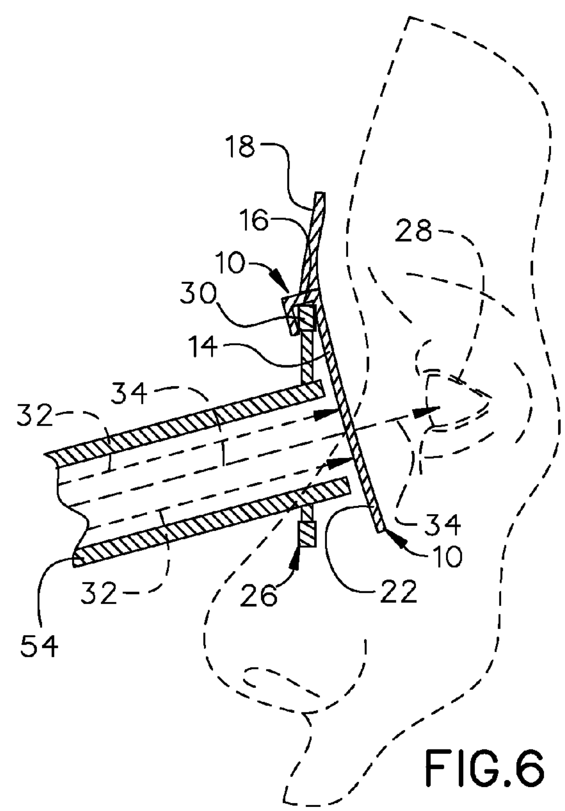
FIG. 6 is a section detail view of the present invention along line 6-6 in FIG. 2.

Referring to FIGS. 1 through 8, the present invention includes an eyewear filtering insert 10. The filtering insert 10 includes a first filter lens 14 and a second filter lens 14, each having an inner surface and an outer surface. The first and second filter lens 14 are comprised of an electromagnetic filter 22. The present invention further includes a bridge connector 20. The bridge connector 20 connects the first and second filter lenses 14 together. The bridge connector 20 includes medial protective barriers 50 extending downward to increase the protection of the eyes 28. The bridge connector 20 further includes a curved inner edge formed to fit around the nose piece of the eyewear. Therefore, as in FIGS. 1 and 6, a user 24 may wear a pair of prescriptive, protective, or magnifying eyewear 26 and may place the filtering insert 10 in between the eyewear 26 and the user, thereby shielding the user from electromagnetic energy 32. FIG. 6 further illustrates the angulation of the filter lenses 10 relative to the eyewear 26 which creates a recess of space for the telescopes 54 which protrude through the eyewear 26.

In certain embodiments, the present invention may include a variable number of resting tabs 16 to secure the filtering insert 10 to the eyewear 26. The resting tabs 16 may extend from an edge of the filtering insert 10 and protrude past the outer surfaces of the first and second filter lens 14 forming a channel appropriately sized to secure over an eyewear frame 30. Certain embodiments may project these resting tabs 16 laterally to rest on the arms of the eyewear (not shown). In certain embodiments, the present invention includes a first resting tab 16 extending from the top edge of the first filter lens 14 and a second resting tab 16 extending from the top edge of the second filter lens 14. More than one resting tab 16 further secures the filtering insert 10 to the protective eyewear 26. In certain embodiments, the present invention includes grasping tabs 18 protruding upwards and slightly forward from each of the first and second filter lenses 14. Therefore, as seen in FIG. 1, a user 24 may easily affix the filtering insert 10 behind the eyewear 26 by the grasping tabs 18.

Other than the resting tabs 16, the present invention may include additional fastening methods to improve adherence of the filtering insert 10 to the eyewear frame 30.

Figure 7:
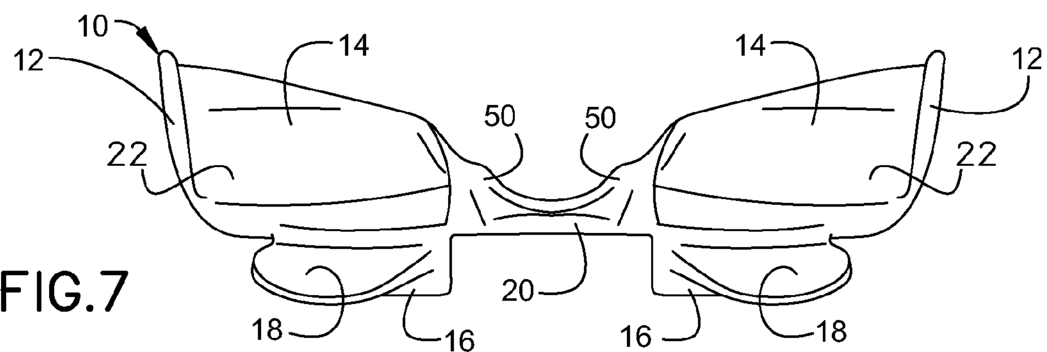
FIG. 7 is a top view of an alternate straight embodiment of the present invention.
Figure 8:
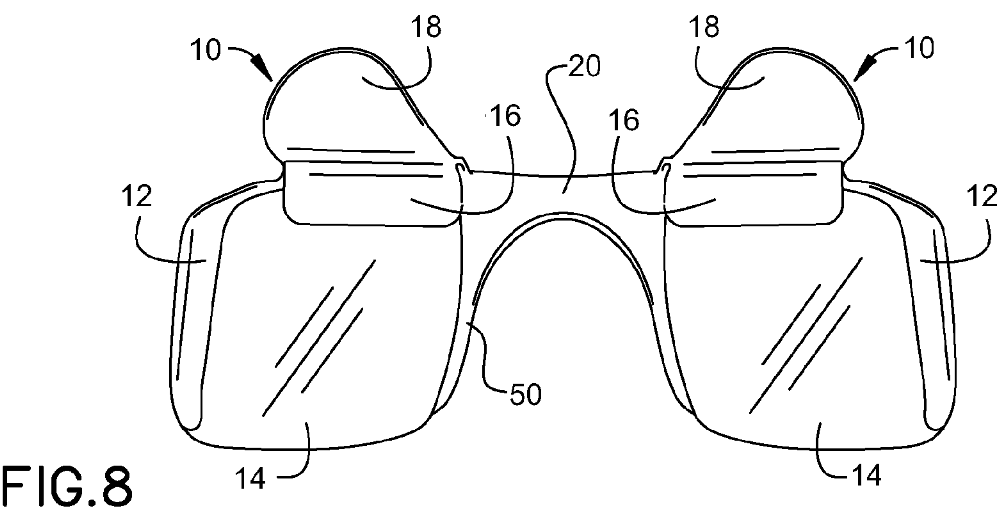
FIG. 8 is a front view of an alternate straight embodiment of the present invention.

In certain embodiments, the first and second filter lenses 14 may be substantially curved away from the resting tabs 16. Therefore, as mentioned above, and illustrated in FIGS. 3 and 4, the lenses 14 may be curved to fit in between the user's curved eyewear 26 and the user 24. However, as illustrated in FIGS. 7 and 8, the filter lenses 14 may be substantially straight to fit non-curved eyewear 26. The present invention further includes lateral protective barriers, or side wraps 12, extending from each side of the first and second filter lenses 14. The lateral protective barriers cover the side of the user's eye 28, thereby providing full protection from the electromagnetic energy 32.

As mentioned above, the first and second filter lenses 14 may be made of a transparent plastic, a transparent glass or a combination thereof. In certain embodiments, various different colors of the present invention may be utilized to filter, absorb and protect against different wavelengths of electromagnetic energy 32 or to selectively filter, thus enabling screening and diagnostic usage. A few examples of electromagnetic frequencies that currently require eye protection include but are not limited to: lasers at 810 Nm, 940 Nm, 980 Nm 1,064 Nm, 2780 Nm, 2,940 Nm, 10,600 Nm, as well as composite or curing lights or lasers in the 500 Nm range and the like. As illustrated in FIG. 6, the filter lenses 14 may prevent electromagnetic energy 32 from passing through lens telescopes 54 of protective eyewear 26 and into the user's eyes 28. However, light 34 may still pass through the filter lenses 14.

The present invention may be placed between eyes and the lenses of protective, prescriptive, magnification or light-bearing eyewear. In alternate embodiments, the present invention may also be affixed to the external surface of existing eyewear depending upon the mechanics involved in each embodiment of the present invention. In certain embodiments that include the resting tabs and grasping tabs, the user may grasp the filtering insert by one of the grasping tabs with the thumb and index finger of one (either) hand, and may slide the resting tabs over the frame of the eyewear so that the frame is secured within the channel, thereby securing the filtering insert to the users eyewear without removing the eyewear. Gravity, resting tabs, the forward slope of the cheeks, and the medial and lateral protective barriers all help to stabilize and keep the filters in place.

The present invention may be used to completely or partially filter electromagnetic radiation for either full protection or specific selective filtration usages. Examples of selective filtration applications may include but are not limited to oral, gynecological and other visual examination screening of tissues for dysplastic, pre-cancerous or cancerous change as well as using selective electromagnetic filtration techniques for industrial design and or non-destructive evaluation of strength and potential weaknesses of vital assemblies within materials that may be in use or proposed for use in industrial, building, scientific and or military applications.

A method of manufacturing the present invention may include the following. Digital design files may be fabricated to represent each version of the present invention. These design files may be typically started by laser scanning the most commonly worn eyewear used in fields utilizing radiation emitting devices (dentistry, medicine, industrial, government, military, etc.) For examples, prescription lenses, magnification loupes or telescopes as well as work area light sources or fiber optics and any other form of eyewear commonly used in conjunction with radiation emitting devices may be scanned. These scanned devices enable designers to digitize the dimensions for each type of commonly employed eyewear that may then be used to create a custom fit of the present invention. After customization by adding upper right and upper left grasping tabs for ease of placement and removal, along with adding resting tabs or any other types of attachment(s) to assist with stabilization for each type of eyewear is finalized; the digital files of the present invention may be utilized to program injection molding machines to form each shape needed for every alternative embodiment of the present invention. A similar method may be used with a 3-d printer.

In certain embodiments, the present invention may be disposable filters for biological protection such as visors, chemical splash guards, helmets or any other application where cheap, lightweight radiation eye protection is preferred. Furthermore the present invention may be used with visor inserts for healthcare or other professions using lasers, hazmat suits, space suits, flight suits, scuba suits, wet suits, exoskeletons, heads up displays and in any other situation where cheap lightweight, customizable, potentially disposable, radiation protection is desired.

The transparent or tinted plastic or glass radiation filtering lenses may be custom formed into various shapes depending on what type of eyewear the present invention is to be used with. In certain embodiments, the invention may be made by injection molding in order to fashion plastic radiation filtering lenses that may insert or fit onto a device scanned or modeled from a laser scanned or otherwise fabricated digital file. Different files may be designed, used and stored for on demand manufacturing for each application. Final designs may be fabricated to fit behind already worn eyewear with our inserts utilizing gravity, resting tabs, and the slope of the cheeks to assist with holding the device or filters in place. Medial barriers and lateral barriers may assist with stabilization. Other components of our radiation filters may include, but are not limited to, magnets, adhesive strips, Velcro®, ball and socket or clip type attachments. In alternative embodiments, the present invention may be designed into a visor type face-shield and/or placed on the outside (instead of the inside) of existing eyewear that operators are already wearing and that could benefit from a lightweight, inexpensive radiation filtering device.

The present invention includes a radiation filtering or partial filtering device, which rests on the user's eyewear between his eyes and the radiation source. The present invention may either protectively filter out harmful electromagnetic radiation or selectively filter radiation in a manner that is useful for screening cancers or pre-cancerous and dysplastic tissues as well as for screening the strength or fatigue of industrial building materials or evaluating the quality of materials on already built machinery such as non destructive testing of airplanes, submarines, buildings and any other object in which evaluation of the sub materials strength may be useful. The filtering inserts of the present invention do not need to use metal clamps for retention but instead may use gravity, resting tabs and the natural slope of the cheeks as well as medial and lateral protective barriers to help stabilize and retain the inserts in their optimal position. Additionally, the inserts of the present invention may have right and left grasping tabs which enable users to grasp the filters with only the thumb and index finger of one (either) hand and passively guiding them into or out of position without necessitating removal of eyewear or other equipment. The present invention may greatly reduce time and frustration exemplified by the prior art, as well as greatly reducing risks of infectious disease cross contamination. In addition, these filters are simpler, lighter, less expensive, more varied in their scope and function; as well as far more comprehensive in performing eye protection and diagnostic procedures due to their ease of customization and selective filtration options.

It should be understood, of course, that the foregoing relates to exemplary embodiments of the invention and that modifications may be made without departing from the spirit and scope of the invention as set forth in the following claims.

What is claimed is:

1. A filtering insert comprising:

a first electromagnetic filter lens comprising an inner surface and an outer surface;

a second electromagnetic filter lens comprising an inner surface and an outer surface;

a bridge connector connecting the first electromagnetic filter lens and the second electromagnetic filter lens, and comprising a curved inner edge formed to fit around a nosepiece of an eyewear;

at least one resting tab extending from an edge of the filtering insert and protruding past the outer surfaces of the first and second electromagnetic filter lenses; and at least one grasping tab extending upward from the at least one resting tab.

2. The filtering insert of claim 1, wherein the first and second electromagnetic filter lenses are curved away from the at least one resting tab and are thereby formed to fit in between the eyewear frame and a user.

3. The filtering insert of claim 1, further comprising a medial protective barrier and a lateral protective barrier extending from each side of the first and second electromagnetic filter lenses and configured to cover sides of a user's eyes.

4. The filtering insert of claim 1, wherein the at least one resting tab comprises a first resting tab extending from a top edge of the first electromagnetic filter lens and a second resting tab extending from a top edge of the second electromagnetic filter lens.

5. The filtering insert of claim 1, wherein the first and second electromagnetic filter lenses are made of a transparent plastic, a transparent glass, or a combination thereof.

6. The filtering insert of claim 1, wherein the at least one resting tab forms a channel sized to receive a frame of the eyewear.

7. The filtering insert of claim 1, wherein the at least one grasping tab comprises a first grasping tab protruding upward from the first resting tab and a second grasping tab protruding upward from the second resting tab.

8. A method of protecting eyes from damage comprising:

placing a pair of eyewear on a user; and placing a filtering insert in between the eyewear and the user, wherein the filtering insert comprises:

a first electromagnetic filter lens comprising an inner surface and an outer surface;

a second electromagnetic filter lens comprising an inner surface and an outer surface;

a bridge connector connecting the first electromagnetic filter lens and the second electromagnetic filter lens;

at least one resting tab extending from an edge of the filtering insert and protruding past the outer surfaces of the first and second electromagnetic filter lenses; and at least one grasping tab extending upward from the at least one resting tab.

9. The method of claim 8, wherein the filtering insert comprises at least one resting tab forming a channel.

10. The method of claim 9, further comprising:

grasping the eyewear filtering insert by the at least one grasping tab; and sliding the at least one resting tab over a frame of the pair of the protective eyewear so that the frame is secured within the channel, thereby securing the filtering insert to the eyewear.

11. A filtering insert comprising:

a first electromagnetic filter lens comprising an inner surface and an outer surface;

a second electromagnetic filter lens comprising an inner surface and an outer surface;

a bridge connector connecting the first electromagnetic filter lens and the second electromagnetic filter lens, and comprising a curved inner edge formed to fit around a nosepiece of an eyewear; and a medial filtering barrier extending downward from said bridge connector and configured to cover a side of a user's eye.

12. The filtering insert of claim 11, wherein the first and second electromagnetic filter lenses are curved and adapted to fit in between an eyewear frame worn by a user and the user.

13. The filtering insert of claim 11, further comprising a lateral protective barrier extending from each side of the first and second electromagnetic filter lenses and configured to cover an opposite side of the user's eye.

14. The filtering insert of claim 11, further comprising at least one first tab extending from the first electromagnetic filter lens, the second electromagnetic filter lens, or both.

15. The filtering insert of claim 14, further comprising at least one second tab extending from the first electromagnetic filter lens, the second electromagnetic filter lens, or both, wherein the second tab extends in a different direction than the first tab.

16. The filtering insert of claim 11, wherein the first and second electromagnetic filter lenses are made of a plastic, a glass or a combination thereof.

* * * * *